United States Patent [19]

Sano et al.

[11] 4,379,741
[45] Apr. 12, 1983

[54] OXYGEN CONCENTRATION SENSOR

[75] Inventors: Hiromi Sano, Nagoya; Masatoshi Suzuki, Anjo, both of Japan

[73] Assignee: Nippondenso Co., Ltd., Kariya, Japan

[21] Appl. No.: 281,855

[22] Filed: Jul. 9, 1981

[30] Foreign Application Priority Data

Jul. 11, 1980 [JP] Japan .................................. 55-95250

[51] Int. Cl.³ ............................................. G01N 27/58
[52] U.S. Cl. .................................... 204/424; 204/429
[58] Field of Search ............................ 204/195 S, 1 S

[56] References Cited
U.S. PATENT DOCUMENTS 4,096,048 6/1978 Matsumoto et al. ............ 204/195 S
4,253,302 3/1981 Asano et al. ................ 204/195 S X

FOREIGN PATENT DOCUMENTS 54-13395 1/1979 Japan ................................ 204/195 S Primary Examiner—G. L. Kaplan
Attorney, Agent, or Firm—Cushman, Darby & Cushman

[57] ABSTRACT

An oxygen concentration sensor is provided for sensing a concentration of oxygen in a sensing gas, in which a solid reference material acting as a solid pole is housed within a container on the inner surface of which an electrode is provided. A sealing material having an output terminal is located to seal the entrance of the container so as to electrically connect the inner surface electrode to the output terminal through the sealing material.

5 Claims, 5 Drawing Figures

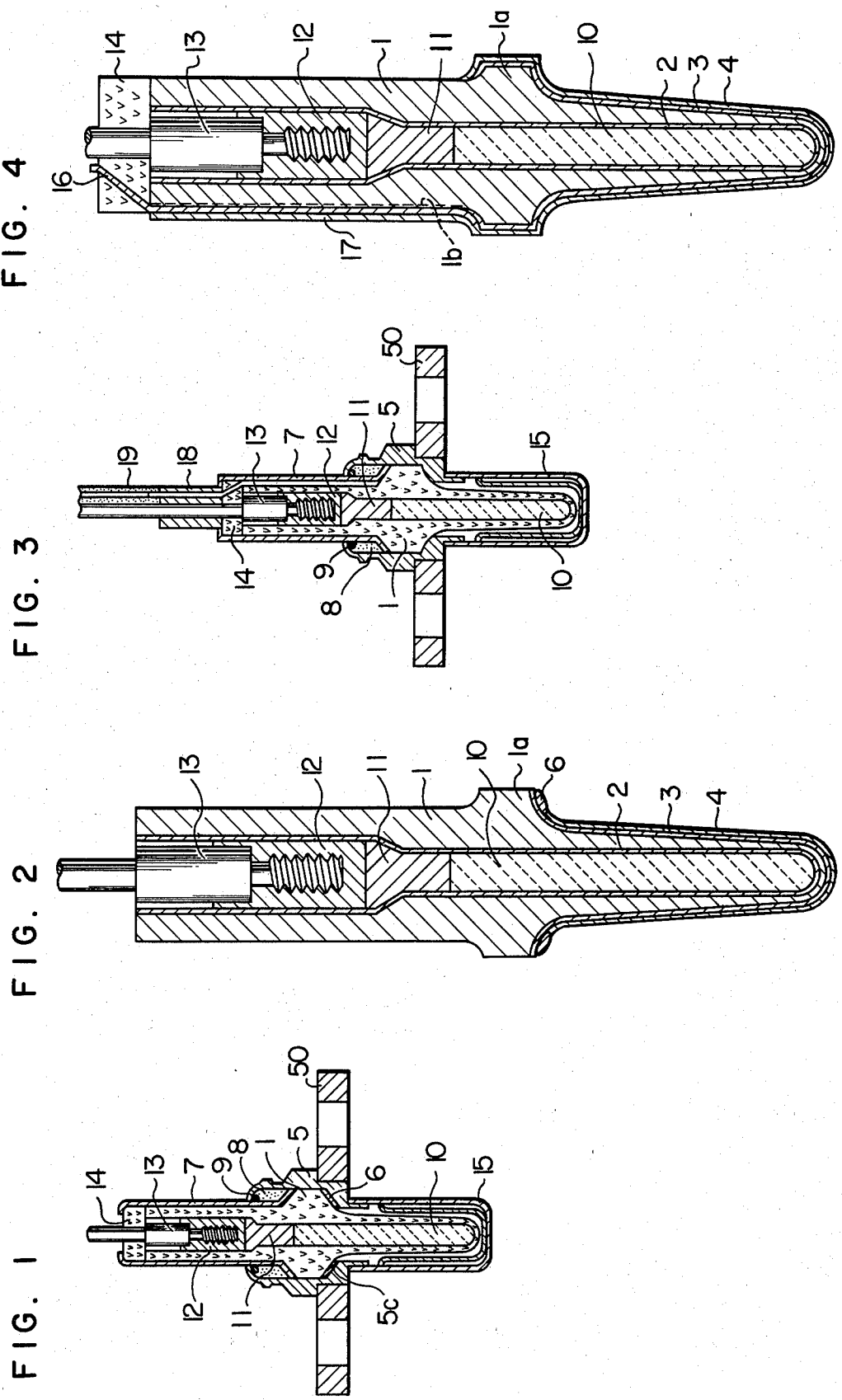

OXYGEN CONCENTRATION SENSOR

BACKGROUND OF THE INVENTION

The present invention relates to an oxygen concentration sensor for sensing the concentration of oxygen in an exhaust gas of an internal combustion engine, for example, and more particularly a sealing structure and a structure for leading out an electrode in the oxygen concentration sensor using a solid reference material as a reference oxygen partial pressure sensor.

In a prior oxygen concentration sensor with the solid reference material of this kind, the solid reference material has been used, as just mentioned. In the sensor, how to stably seal the solid reference material over a long period of time is an important problem. How to lead out an electrode located on the solid reference material side simply is another important problem.

Actually, however, there has never been any proposal to solve the above problems.

SUMMARY OF THE INVENTION

In the light of the above problems, the present invention is proposed and has an object to provide an oxygen concentration sensor with a simple structure which can seal a solid pole made of solid reference material stably over a long period and can lead an electrode on the solid pole side to the exterior.

BRIEF DESCRIPTION OF THE DRAWINGS

FIG. 1 is a longitudinal cross sectional view of an embodiment of an oxygen concentration sensor according to the present invention.

FIG. 2 is a longitudinal cross sectional view of a leading portion of the sensor shown in FIG. 1.

FIG. 3 is a longitudinal cross sectional view of a modification of the sensor shown in FIG. 1.

FIG. 4 is a longitudinal cross sectional view of a leading portion of the sensor shown in FIG. 3.

DESCRIPTION OF THE PREFERRED EMBODIMENT

Figure 5:
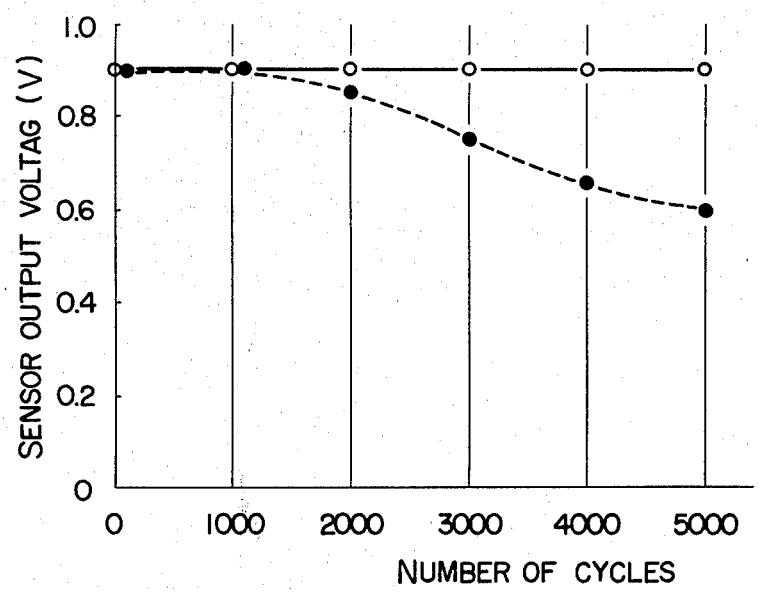
FIG. 5 illustrates characteristic curves useful in explaining the effect of the present invention.

The present invention will be described in detail based on embodiments thereof. In FIGS. 1 and 2, reference numeral 1 designates a solid electrolyte member for sensing an oxygen concentration. The solid electrolyte member 1 is made of an oxygen ion conductive metal oxide of a solid solution of 95 mol % of zirconium oxide and 5 mol % of yttrium oxide. The solid electrolyte member is shaped like a cup of which one end is closed and the other end is open. First and second electrodes 2 and 3 made of platinum or of a platinum family metal acting as a catalyst are formed on the inner and outer periphery surfaces of the solid electrolyte member 1 by applying a chemical plating, vacuum deposition, paste baking, or applying an electric plating onto a chemical plating. Formed on the outer surface of the second electrode 3 is a heat-resistive and porous film 4 made of magnesia alumina spinell or the like.

Reference numeral 5 designates a tubular housing made of heat resistive metal to which a flange for fixing it to an exhaust pipe is fixed by welding. A ring-like expanded portion 1a of the solid electrolyte member 1 is placed on a tapered seat 5c on the inside of the housing 5, with a heat resistive metal packing 6 of copper, nickel or the like interposing therebetween. The second electrode 3 of the solid electrolyte member 1 is electrically connected to the housing 5 (SUS304) through the packing 6. A space between a metal cover 7 around the entire periphery of the solid electrolyte member 1 and the housing 5 is filled with talc powder 8. A metal calking ring 9 is disposed around the upper portion of the talc powder filled section. By radially calking the upper end of the housing 5, the solid electrolyte member 1 is pushed downwardly, so that the tapered surface of the ring like, expanded portion 1a of the solid electrolyte member 1, is pressed against the packing 6 of the housing 5. In this way, the solid electrolyte member 1 is fixed so as not to be moved.

A hollowed portion of the solid electrolyte member 1 is filled with a solid rod 10 made of solid standard material having reference oxygen partial pressure characteristic, such as mixed powder of metal of the iron family, (for example, iron, nickel, cobalt or the like), and ceramics, (for example, alumina zirconia), or a mixed powder of a metal of the iron family and the oxide of the iron family metal. A cylindrical metal stop 11 made of metal, for example, is provided above the solid rod 10. Reference numeral 12 is conductive glass sealing material prepared in a manner such that a mixed powder of 50 to 65 wt % of copper powder, 25 to 40 wt % of borosilicate glass, and 2 to 10 wt % of silicon, is wetted with dextrin solution, and the wet mixed powder is melted and solidified. In a specific method, the mixed pwder, being wetted with dextrin solution, fills a space above the metal stop 11, the mixture is hardened by thrusting it with a metal stick, a metal terminal 13 is screwed into the hardened mixture and finally the hardened mixture is heated to 850° C. As the mixture softens, the terminal 13 is pushed into the mixture softened and then is cooled. As a result of this processing, a conductive glass sealing material is formed, while at the same time the lead-out function of the inner electrode 2 is performed. Reference numeral 14 designates an alumina ring plate which is placed on the upper portion of the terminal 13. The upper end of the metal cover 7 is pressed against the ring plate 14 to form a unit body. Incidentally, the terminal 13, the solid electrode member 1 and the sealing material are so selected as to have substantially equal coefficients of thermal expansion. A metal protecting cover 15, forming a double structure for preventing the solid electrolyte member 1 from directly contacting the exhaust gas, is fixed to the housing 5 by welding.

The operation of the oxygen concentration sensor thus constructed will now be described. Since the conductive glass seal material 12 is located at the portion of the solid electrolyte member 1 on the atmosphere side, it is hardly influenced by the heat of the exhaust gas. Therefore, it is a rare case that the sealing material is softened and changed in quantity to deteriorate the sealing effect of the solid pole 10. Further, the conductive glass sealing material 12 is conductive to the letter of its name. With this nature, the electrode 2 on the inner side of the solid electrolyte member 1 is electrically connected to the terminal 13 through the sealing material 12, with the result that the lead-out work of the electrode 2 to exterior and the sealing of the solid pole 10 are simultaneously attained by the conductive glass sealing material 12.

Then, an oxygen density sensor, which is an embodiment of the present invention, and a sensor to be compared in which the sealing material 12 (not containing copper powder) is placed on the portion of the solid electrolyte member 1 on the exhaust gas side, were prepared. By using the sensors, sealing performances of the solid poles 10 of both the sensors were experimentally checked. The results of the experiment are shown in FIG. 5. For testing the endurance conditions, both sensors were mounted to an exhaust pipe of an internal combustion engine of a total displacement of 2000 cc and a cool-heat cycle, 850° C.-normal temperature (10 minutes of holding time) of the exhaust gas. This procedure was repeated for 5000 cycles. An evaluation condition was measured in a manner that the standard gas of the excess coefficient of 0.9 (reduction atmosphere) is applied to the sensors and the output voltages of the sensors at that time were measured at every cool-heat cycle.

As seen from FIG. 5, the sensor of the present invention has an output voltage remaining exactly at its initial value, even after the endurance test of 5000 cycles and the sealing effect on the solid pole 10 is kept stable. On the other hand, in the comparative sensor to be measured, the output voltage falls off in the vicinity of 2000 cycles and its durability is poor.

FIGS. 3 and 4 cooperatively show a modification of the above-mentioned embodiment according to the present invention. In the present embodiment, a groove 1b is formed on the outer surface of the solid electrolyte member 1 and a lead wire 16 of a platinum wire is fitted in the groove 1b. The lead wire 16 is bonded by ceramic adhesive 17. The lead wire 16 extends along the side of the terminal 13, through the ring plate 14, and is electrically insulated by a covering member 18 of Teflon resin. Reference numeral 18 designates an insulating covering member for the lead wire 16.

While in the above-mentioned embodiments the solid electrolyte member 1 is formed like a cup, thereby forming the container by itself, the container may be formed in a manner that the solid electrolyte member 1 is formed planar and an alumina ceramic tube or a metal tube is hermetically mounted to the planar solid electrolyte member 1. The metal powder contained in the conductive glass sealing material 12 may be not only copper powder but also iron powder or the like.

As described above, in the present invention, it is possible to realize a stable seal of the solid pole over a long period of time and the lead-out work of the innner electrode simultaneously.

We claim:
1. An oxygen concentration sensor comprising:
   a generally cup-shaped sensing element of a solid electrolyte member having an open end and a closed end;
   first and second electrodes provided on the inner and outer surfaces of said sensing element;
   a solid rod made of solid reference material having a reference oxygen partial pressure characteristic and disposed on the closed end of said sensing element;
   an electrically conductive sealing material element located at the upper portion of said sensing element adjacent to the open end of said sensing element, said sealing material element being a melted and solidified mixture of metal powder and glass powder; and
   a metal terminal supported by and partially embedded into said sealing material element to electrically connect said first electrode with said terminal through said sealing material element.

2. An oxygen concentration sensor according to claim 1 wherein the solid electrolyte member of said sensing element is made of an oxyen ion conductive metal oxide consisting of a solid solution of 95 mol % of zirconium oxide and 5 mol % of yttrium oxide.

3. An oxygen concentration sensor according to claim 1 wherein said first and second electrodes are made of platinum or a platinum family member catalyst made of platinum or a platinum family member.

4. An oxygen concentration sensor according to claim 1 wherein the solid reference material of said solid pole includes mixed powder of metal of an iron family and ceramics, or mixed powder of metal of the iron family and the oxide of the iron family metal.

5. An oxygen concentration sensor according to claim 1 wherein said electrically conductive glass sealing material element includes a melted and solidified mixture of 50 to 65 wt % of copper powder, 25 to 40 wt % of borosilicate glass and 2 to 10 wt % of silicon.

* * * * *